United States Patent
Andrews et al.

(10) Patent No.: US 7,846,106 B2
(45) Date of Patent: Dec. 7, 2010

(54) ATRIAL FIBRILLATION DETECTION USING SPO2

(75) Inventors: Angela Andrews, Waukesha, WI (US); Bruce Friedman, Tampa, FL (US); Donald Brodnick, Cedarburg, WI (US); George Hutchinson, Milwaukee, WI (US)

(73) Assignee: The General Electric Company, Schenectady, NY (US)

( * ) Notice: Subject to any disclaimer, the term of this patent is extended or adjusted under 35 U.S.C. 154(b) by 1202 days.

(21) Appl. No.: 11/411,714

(22) Filed: Apr. 26, 2006

(65) Prior Publication Data

US 2007/0255146 A1  Nov. 1, 2007

(51) Int. Cl.
*A61B 5/02* (2006.01)

(52) U.S. Cl. .................................................. 600/500

(58) Field of Classification Search ............... 356/39; 600/17, 301, 438, 484, 500, 508, 509, 513, 600/516, 518, 514, 490, 341; 604/14, 17, 604/19; 607/6
See application file for complete search history.

(56) References Cited

U.S. PATENT DOCUMENTS

| | | | |
|---|---|---|---|
| 4,262,674 A | | 4/1981 | Vemura et al. |
| 4,356,827 A | | 11/1982 | Vemura et al. |
| 5,152,296 A | | 10/1992 | Simons |
| 5,404,878 A | | 4/1995 | Frankenreiter et al. |
| 5,865,756 A | * | 2/1999 | Peel, III ........................ 600/490 |
| 5,931,790 A | | 8/1999 | Peel, III |
| 6,122,536 A | * | 9/2000 | Sun et al. ...................... 600/341 |
| 6,188,470 B1 | * | 2/2001 | Grace .......................... 356/39 |
| 6,423,010 B1 | | 7/2002 | Friedman et al. |
| 6,477,406 B1 | | 11/2002 | Turcott |
| 6,485,429 B2 | | 11/2002 | Forstner |
| 6,490,479 B2 | | 12/2002 | Bock |
| 6,491,638 B2 | | 12/2002 | Oka |
| 6,491,639 B1 | * | 12/2002 | Turcott ........................ 600/508 |
| 6,496,723 B1 | | 12/2002 | Kawachi et al. |
| 6,600,949 B1 | * | 7/2003 | Turcott ........................ 600/518 |
| 6,719,701 B2 | | 4/2004 | Lade |

(Continued)

FOREIGN PATENT DOCUMENTS

JP    5200005 A2    8/1993

(Continued)

OTHER PUBLICATIONS

Paula S. McKinley et al., "Deriving Heart Period Variability from Blood Pressure Waveforms,"; Jun. 27, 2003; J. Appl Physiol. 95: 1431-1438.

(Continued)

*Primary Examiner*—George Manuel
*Assistant Examiner*—Robert N Wieland
(74) *Attorney, Agent, or Firm*—Sceales, Starke & Sawall, LLP (57) ABSTRACT

The method and system includes detecting atrial fibrillation in a patient by monitoring the blood oxygen saturation level over a period of time. The method and system produces a plethysmographic waveform from the monitored blood oxygen saturation level and analyzes the plethysmographic waveform and detected intervals and determines whether the patient is in atrial fibrillation. The method and system is preferably implemented in a software application and may be configured to report to the user on the current state of atrial fibrillation (AFIB) and a current trend.

26 Claims, 6 Drawing Sheets

U.S. PATENT DOCUMENTS

| | | | |
|---|---|---|---|
| 7,074,192 | B2 | 7/2006 | Friedman et al. |
| 7,532,929 | B2* | 5/2009 | Mussig et al. ............... 607/14 |
| 2002/0183631 | A1 | 12/2002 | Park |
| 2003/0040675 | A1 | 2/2003 | Sharrock |
| 2003/0097158 | A1 | 5/2003 | Belalcazar |
| 2005/0004477 | A1 | 1/2005 | Friedman et al. |
| 2005/0015009 | A1* | 1/2005 | Mourad et al. ............. 600/438 |
| 2007/0255146 | A1 | 11/2007 | Andrews et al. |
| 2008/0183093 | A1* | 7/2008 | Duann et al. ............... 600/516 |
| 2008/0200819 | A1 | 8/2008 | Lynn et al. |
| 2009/0012412 | A1* | 1/2009 | Wiesel ...................... 600/508 |
| 2009/0149751 | A1* | 6/2009 | Mourad et al. ............. 600/438 |

FOREIGN PATENT DOCUMENTS

| | | | |
|---|---|---|---|
| JP | 5212004 | A2 | 8/1993 |
| JP | 5288869 | | 11/1993 |
| JP | 5288869 | A2 | 11/1993 |
| JP | 8089484 | A2 | 4/1996 |
| JP | 2001029318 | A2 | 2/2001 |
| JP | 2002272689 | A2 | 9/2002 |
| JP | 23210420 | A2 | 7/2003 |
| WO | 2006093699 | | 9/2006 |

OTHER PUBLICATIONS

N.D. Giardino et al., "Comparison of Finger Plethysmograph to ECG in the Measurement of Heart Rate Variability," *Psychophysiology*, Mar. 2002; 39(2): 246-53.

S. Carrasco et al., "Comparison of the Heart Rate Variability Parameters Obtained from the Electrocardiogram and the Blood Pressure Wave," *Journal of Medical Engineering Technology*. Sep.-Oct. 1998; 22(5):195-205.

Murthey, V.S. et al. (2001) "Analysis of photoplethysmographic signals of cardiovascular patients," 2001 Proceedings of 23rd Annual EMBS International Conference, Istanbul, Oct. 25-28, 2001, pp. 2204-2207.

* cited by examiner

ATRIAL FIBRILLATION DETECTION USING SPO2

FIELD OF THE INVENTION

The invention relates to the field of patient monitoring. More particularly, the invention relates to the field of patient monitoring to detect atrial fibrillation.

BACKGROUND OF THE INVENTION

Monitoring of chronically ill patients in the home environment will become more common in the near future as the population ages, health care costs increase and patients demand more control over their own care. The clinical data collected in the home, such as blood pressure, weight, and heart rate can be transmitted back to a caseworker or clinician who can provide early intervention to prevent re-hospitalizations. Many of the patients with chronic illnesses could benefit from home cardiac monitoring.

One very typical and dangerous arrhythmia is atrial fibrillation (AFIB). AFIB is the most common cardiac arrhythmia resulting in hospitalization in the United States. AFIB is identified by irregular heart rhythms and is clinically defined as uncoordinated contractions of the atria. Patients often experience palpitations and have an increased risk of stroke. Some patients may be asymptomatic. Approximately one-third of all strokes are due to AFIB. Furthermore, the presence of AFIB makes strokes 5-times more likely and 2-times more debilitating.

AFIB requires aggressive treatment. The longer a patient is in AFIB, the more likely they are to remain in AFIB, making early detection desirable. Prompt detection of the onset of AFIB provides an opportunity for therapy during the first 48 hours when expensive antithrombotic treatments may not be necessary because the formation of blood clots has not yet occurred in the atria.

Current methods of detecting AFIB are primarily reliant on the use of continuous ECG recordings. Unfortunately, continuous cardiac monitoring via ECG presents many challenges, including the precise application of a variety of electrodes, an uncomfortable apparatus and cabling, and issues with battery replacement. For many patients this level of acuity is not warranted. It would be desirable to be able to screen for AFIB simply, without requiring electrodes or additional sensors.

SUMMARY OF THE INVENTION

The method and system includes detecting atrial fibrillation in a patient by acquiring a plethysmograph waveform from a blood oxygen saturation level monitoring device. The plethysmograph waveform is analyzed and pulse intervals are calculated to determine whether the patient is in atrial fibrillation. The method and system is preferably implemented in a software application and is configured in a report to the patient and/or clinician on the current state of atrial fibrillation (AFIB) and a current AFIB trend.

In one aspect of the present invention, a method of detecting atrial fibrillation in a human or animal subject comprises acquiring a plethysmographic waveform of a patient from a monitoring device over a period of time, measuring a set of pulse intervals from the plethysmographic waveform, measuring a set of features from the plethysmographic waveform and analyzing the set of pulse intervals and the set of pulse features from the plethysmographic waveform to determine an atrial fibrillation state of the patient and wherein the monitoring device is a pulse oximeter sensor and one of the set of features is a set of pulse amplitudes.

This method further comprises analyzing the set of pulse intervals and the set of pulse features from the plethysmographic waveform to detect an atrial fibrillation trend of the patient and reporting the atrial fibrillation trend, and further reporting the atrial fibrillation state. The method also comprises analyzing the set of pulse intervals, which includes: conducting a hidden Markov model analysis on the set of pulse intervals; and conducting a contextual analysis on the set of pulse intervals and wherein the hidden Markov model analysis determines a probability of the patient having an irregular heart rhythm and the contextual analysis rules out atrial fibrillation as a source of irregular heart rhythm.

Analyzing the set of pulse features in this method also includes calculating amplitude variation between each consecutive one of the set of pulse amplitudes, wherein the atrial fibrillation state determination is dependent on an analysis of pulse amplitude variation, and analyzing the set of pulse amplitudes includes determining a set of filling time dynamics of the set of pulse amplitudes and further wherein the steps of analyzing the set of pulse amplitudes and determining the set of filling time dynamics provides an indication of the degree of atrial augmentation present.

In another aspect of the present invention, a system for detecting atrial fibrillation in a human or animal subject comprises a remote sensing system configured to analyze a plethysmographic waveform from a monitoring device, a storage media for storing a computer application, a processing unit coupled to the remote sensing system and the storage media, and configured to execute the computer application, and further configured to receive the plethysmographic waveform from the remote sensing system, wherein when the computer application is executed, a set of pulse intervals from the plethysmographic waveform are detected and a set of pulse features are measured from the plethysmographic waveform, and further wherein the set of pulse intervals and the set of pulse features are analyzed to determine an atrial fibrillation state of the patient. The monitoring device is a pulse oximeter sensor, and when the set of pulse intervals and the set of pulse features from the plethysmographic waveform are analyzed, an atrial fibrillation trend of the patient is detected, and a means for reporting the atrial fibrillation trend to the patient and a means for reporting the atrial fibrillation state are included. When the computer application is executed and the set of pulse intervals is analyzed, a hidden Markov model analysis is conducted on the set of pulse intervals, and a contextual analysis is conducted on the set of pulse intervals, wherein the hidden Markov model analysis determines a probability of the patient having an irregular heart rhythm and the contextual analysis rules out atrial fibrillation as a source of irregular heart rhythm.

In this system, when the computer application is executed and the set of pulse features is analyzed, the filling time dynamics of the set of pulse features is determined, and feature variation between each one of the set of pulse features is calculated relative to the mean, the median, consecutive pulses, or maximum to minimum and wherein the atrial fibrillation state determination is dependent on an analysis of pulse amplitude variation and further wherein the analysis of pulse amplitude variation as a function of filling time provides an indication of the degree of atrial augmentation present.

DETAILED DESCRIPTION OF THE INVENTION

Figure 1:
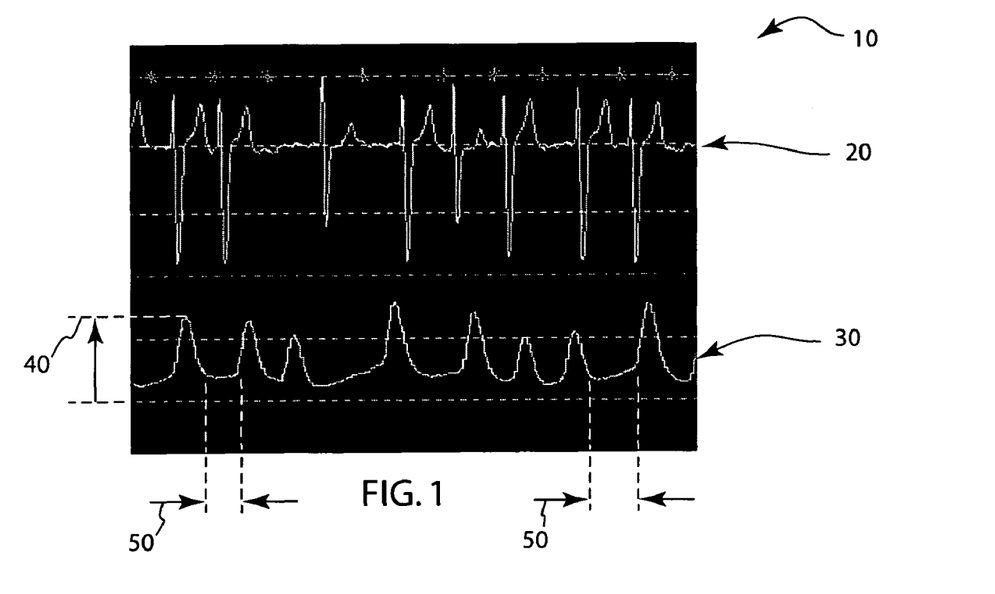
FIG. 1 illustrates a graphical comparison of an ECG wave and a plethysmographic wave.

FIG. 1 illustrates an ECG waveform 20 and a plethysmographic waveform 30. Typically, a physician or healthcare provider will detect and diagnose AFIB in a patient using the ECG waveform 20. However, as discussed above, obtaining an ECG waveform 20 from a patient is much more complex and difficult then obtaining a plethysmographic waveform 30 from a patient. As will be discussed below, in order to detect AFIB using the plethysmographic waveform 30, a number of aspects of the plethysmographic waveform 30 will be examined. A pulse detection will be utilized and the pulse intervals analyzed using a Hidden Markov Model (HMM) method and a contextual analysis. Also, the amplitude 40 of each pulse will be measured and analyzed, as well as the ventricular filling time 50 between each pulse of the plethysmographic waveform. The present invention will allow for a more simplistic and convenient method to detect AFIB using a patient's plethysmographic waveform 30. Of course, this will greatly enhance a home monitoring system as will be described below. The method and system, and implementation of such will be described in greater detail below.

Figure 2:
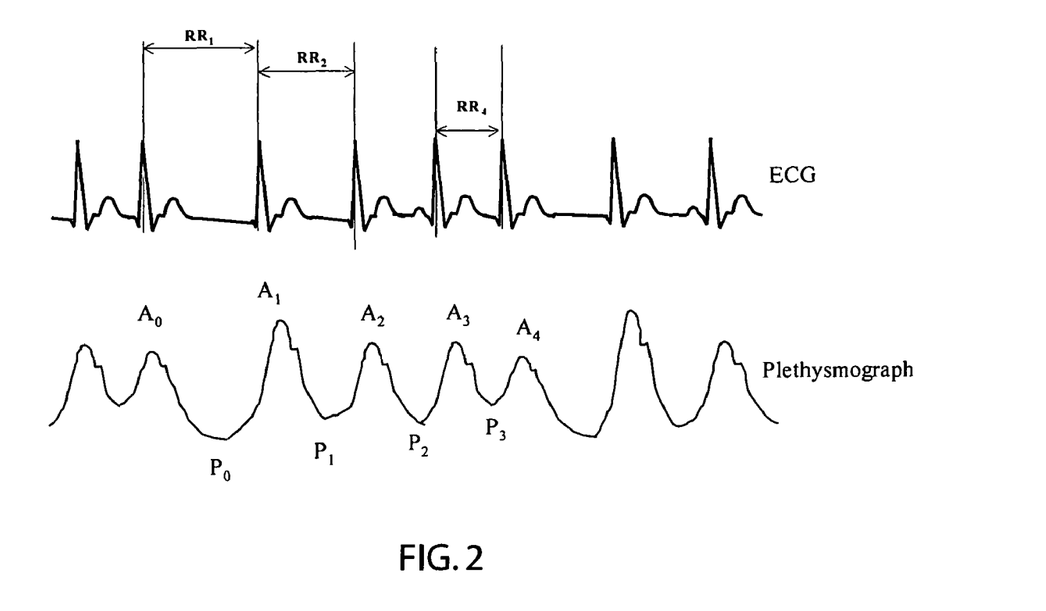
FIG. 2 illustrates an additional graphical comparison of an ECG wave and a plethysmographic wave.

FIG. 2 illustrates the impact of a change in heart rate (or RR interval) on the distal plethysmograph pulse. The interval RR, is longer than the preceding interval that generated pulse $A_0$. As a result, there is more time for the arterial blood to flow passively into the venous system. This produces a lowered blood volume at a diastole ($P_0$). The long RR interval also allows for a longer filing time in the left ventricle of the heart. By Starling's Law, the increased volume in the ventricle results in a more forceful ejection of larger amplitude of the next volume pulse $A_1$.

The following RR interval ($RR_2$) is shorter than the preceding interval. Since there is less time for blood to flow out of the arterial system, the pulse level at $P_1$ does not drop to as low of a value at diastole as the preceding pulse. The short filing time results in a lower stroke volume and a systolic pressure (compared to the preceding interval), which is reflected in the lower amplitude at $A_2$. Interval $RR_4$ illustrates an even shorter interval, with a resulting higher level at $P_2$ and reduced amplitude at $A_4$.

The amplitude of the pulse ($A_{i+1}$-$P_i$) is therefore proportional to the length of the preceding RR interval and can be used as another input to the algorithm used for determining whether a patient is in AFIB.

Figure 3:
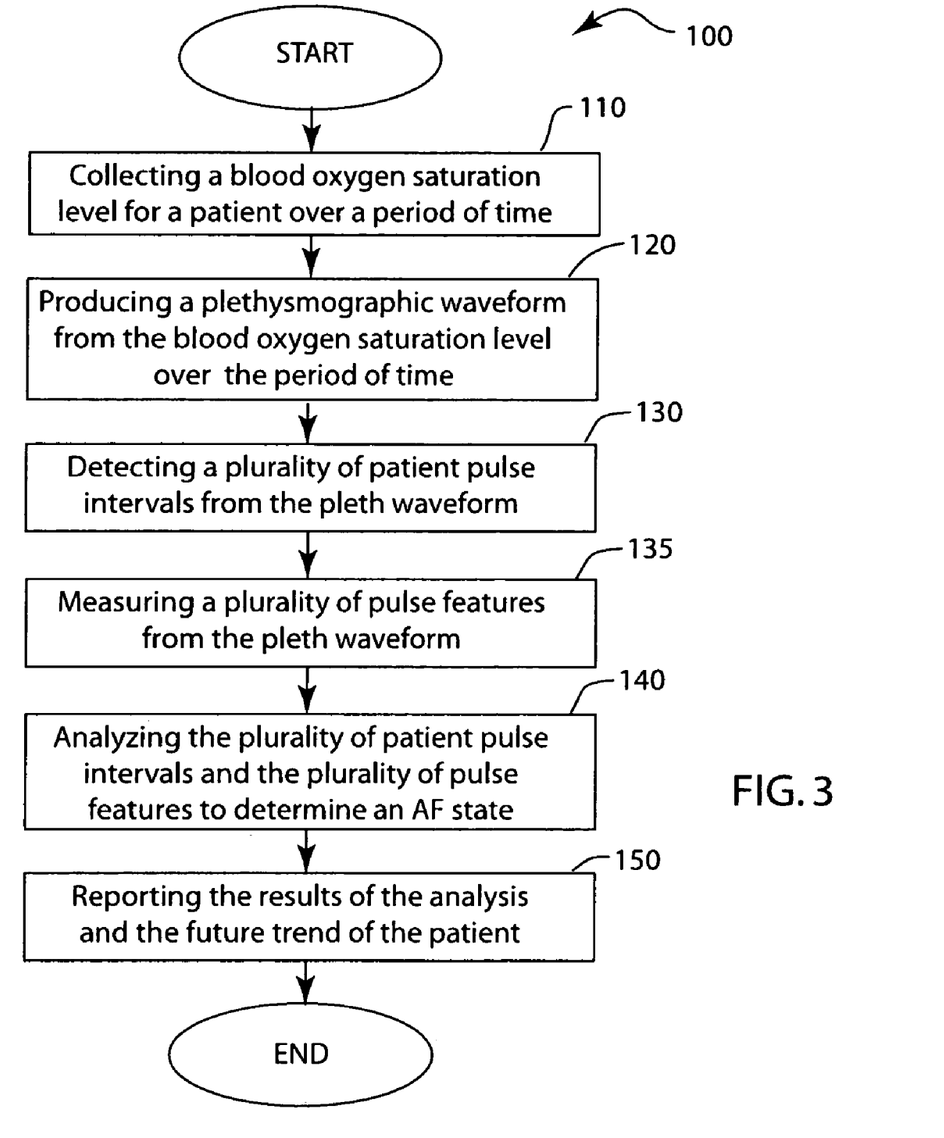
FIG. 3 illustrates a flow chart of a method in accordance with an embodiment of the present invention.

FIG. 3 illustrates a detection method 100 of the present invention. In step 110, the plethysmograph waveform of a patient is collected over a period of time from a plethysmographic sensor. In step 120, the plethysmograph pulses are detected from the plethysmographic waveform over the period of time collected in step 110. A plurality of pulse intervals are detected from the plethysmographic waveform in step 130, and a plurality of pulse features are measured in step 135. The pulse intervals and the pulse features are analyzed to determine an AF state in step 140. The result of the analysis from step 140 are reported in step 150, and a current trend of the patient's AFIB status is also reported.

Figure 4A:
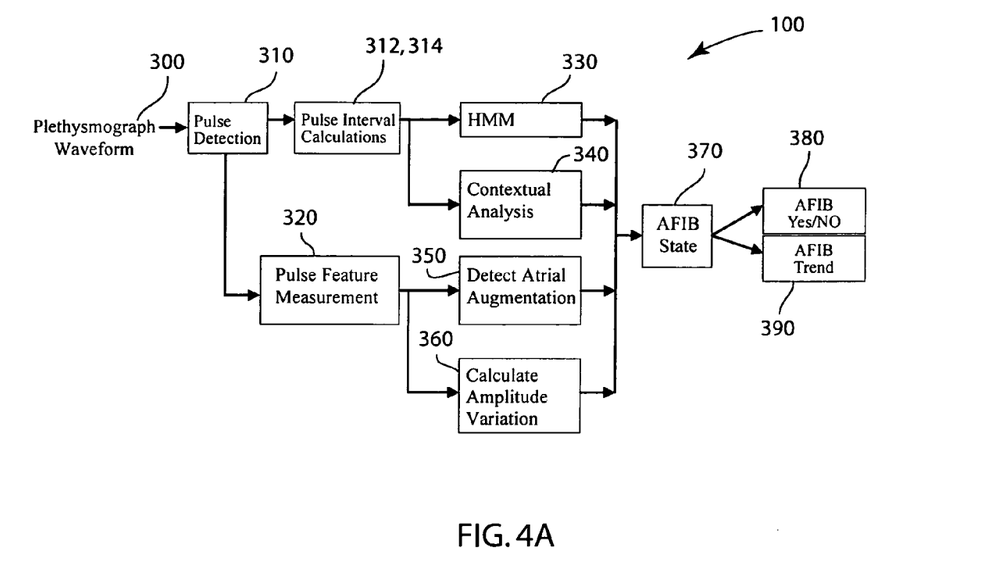
FIGS. 4a-4b illustrate a block diagram of a method in accordance with an embodiment of the present invention.
Figure 4B:
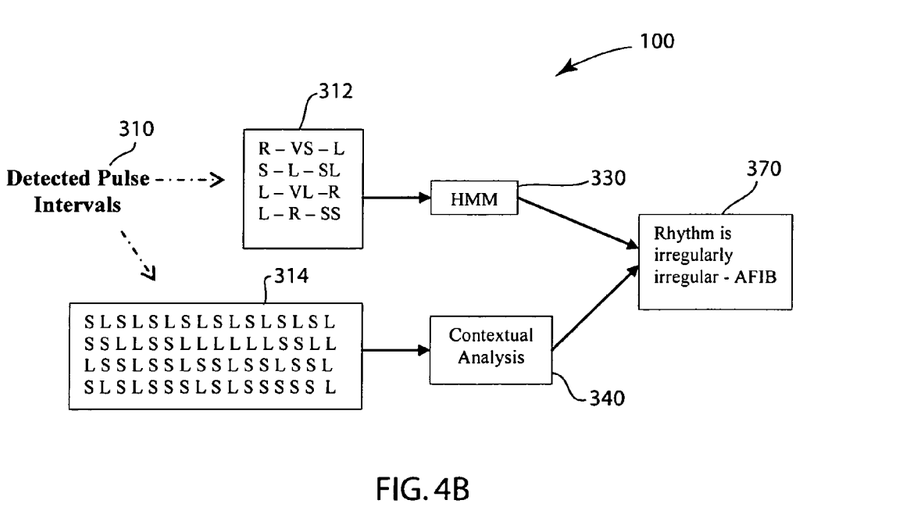

A block diagram of the detecting method 100 is further depicted in FIGS. 4a and 4b. Referring first to FIG. 4a, the SPO2 data is collected and displayed as a plethysmographic waveform 300. Pulse detection 310 is carried out on the plethysmographic waveform 300 which includes detecting a series of pulses and measuring the pulse intervals 312, 314, signifying the repeated filling of the chambers of the heart. Once the pulse detection 310 and pulse interval calculations 312, 314 have occurred, a hidden Markov model (HMM) 330 analysis as well as a contextual analysis 340 may be carried out on the detected pulse intervals. A more detailed description of the HMM 330 and the contextual analysis 340 will be included in the detailed description of FIG. 4b.

Still referring to FIG. 4a, while simultaneously referring to FIG. 1, a pulse feature measurement 320 is conducted on the plethysmographic waveform 300. The pulse feature measurement 320 measures each amplitude 40 of the plethysmographic waveform 30 and utilizes this information to calculate amplitude variation 360. Calculating the amplitude variation 360 gives a physician or healthcare provider an indication of how the heart is operating, and changes in the amplitude of each consecutive pulse, up or down, provide information about the types and regularity.

Figure 5A:
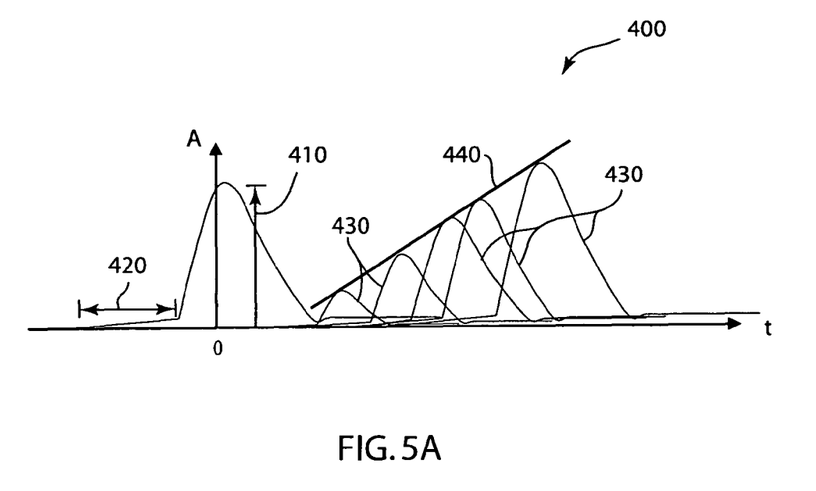
FIGS. 5a-5b illustrate a graphical representation of a slope profile of plethysmographic pulse amplitudes in accordance with an embodiment of the present invention.
Figure 5B:
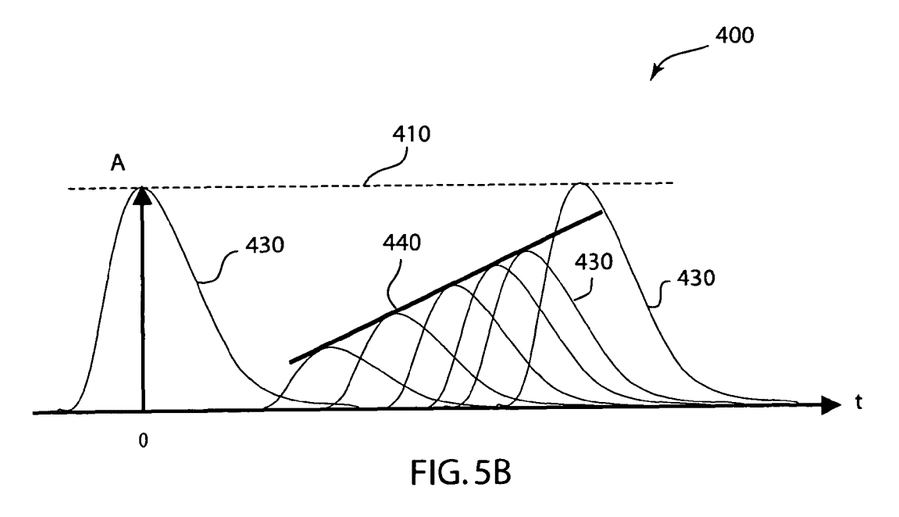

Atrial augmentation detection 350 is also determined using pulse feature measurement 320 data. Referring to FIGS. 4a and 5a-5b simultaneously, the atrial augmentation detection 350 is determined as depicted in FIGS. 5a-5b. The filling time dynamics 400 are important as they can confirm irregularities that may be detected when the amplitude variation is calculated 360. Referring now to FIG. 5a-5b, the filling time dynamics 400 are depicted graphically illustrating time (t) along the x-axis of the graph and amplitude (A) along the y-axis of the graph. The plethysmographic pulse amplitude 410 is highly dependant on ventricular filling time 420. The amplitude slope 440 obtained from a plot of several pulse amplitudes 430 as a function of time provide information about the atrial contribution to cardiac output. The changes in amplitude 410 of the Plethysmographic pulses 430, and the resulting amplitude slope 440 can reflect either the presences or absence of atrial "kick" and relative changes in blood pressure. It should be noted that in FIGS. 5a-5b pulse amplitude 410 and atrial filling time 420 are labeled on a single exemplary pulse waveform, and that each pulse amplitude 430 has an amplitude 410 and filling time 420 value. The resulting filling time dynamic graph 400 is created by "cutting" each individual pulse from the plethysmographic waveform 30 (FIG. 1), including each pulse's atrial fill time 50 and "pasting" each individual pulse on the filling time dynamics graph 400, and starting the fill time 50 at "0".

It is well known that the smaller upper chambers of the heart (left and right atria) when functioning properly push extra blood into the larger lower chambers (left and right ventricles) just prior to each main contraction of the heart. This can account for 10% to 40% of ventricular filling. This augmentation of ventricular filling is missing during atrial fibrillation and accounts for some of the symptoms of these patients. Atrial augmentation is also known as "atrial kick" or "atrial contribution". As people age, the atrial kick becomes more important and so older patients are more affected by atrial fibrillation.

What has not been previously disclosed is a method to recognize in a plethysmographic waveform, evidence of the atrial augmentation. Atrial augmentation can be discerned in the pattern of pulse amplitudes at varying heart beat intervals.

In general the beating of a heart is roughly regular, but a degree of irregularity in rhythm is almost always present. Intervals between heart beats decrease during inspiration of breath. Heart beat intervals lengthen during expiration of breath. Some beats occur early known as premature ventricular complexes (PVC) or premature atrial complexes (PAC) and others. These varying heart beat intervals mean that between heart beats there may be more or less time for blood to fill into the ventricles. Increased filling time results in increased blood ejected and increased blood pressure and an increased pulse amplitude in the plethysmograph for that beat.

Therefore two factors, among others, are affecting plethysmograph amplitude; atrial augmentation and filling time. FIG. 5a illustrates a superimposition of waveforms demonstrating that pulse amplitude increases with filling time. In FIG. 5a, the patient has atrial fibrillation so that the pulse amplitude 410 increases only as a function of filling time 420, and therefore, no atrial augmentation is present.

When atrial augmentation is present the pattern of pulse amplitude 410 at varying heart beat intervals is different. In this case most premature beats will not have the benefit of atrial augmentation and the plethysmograph pulse heights of those beats will be similar to as shown in FIG. 5a. However, at a longer beat interval the atrial augmentation is present and so FIG. 5b shows the increased pulse height of the first and last pulses. These pulses come up to the dotted line shown which is at a level higher than in FIG. 5a.

Therefore the general strategy for recognition of evidence of atrial augmentation is to observe the plethysmograph pulse amplitudes 430 over a period of time including at least some variety of heart beat intervals and observing the degree of pulse height increase as a function of the increase in shorter heart beat intervals. This allows an extrapolation of pulse height as a function of filling time. If atrial augmentation is present, longer heart beat intervals will yield pulse amplitudes exceeding what is expected from filling time alone. FIGS. 5a and 5b are a simplification. The height versus filling time function may not be linear, and the extrapolation may be a more complicated function. However, augmentation is still recognized as a pulse increase over the filling time extrapolation.

Referring back to FIG. 4a the results of the HMM 330, contextual analysis 340, atrial augmentation detection 350, and amplitude variation calculation 360 are evaluated to determine whether the rhythm of the heart is irregular in 370. Whether the patient is an AFIB or not an AFIB is reported in step 380, and a trend of AF 390 during the time period that the plethysmograph was acquired.

Referring now to FIG. 4b, the HMM 330 and contextual analysis 340 will be described in greater detail. In this method 100, the detected pulse intervals 310 are classified as detailed pulse intervals in 312 and as pulse intervals in 314. The HMM 330 and contextual analysis 340 distinguish between rhythms with irregular and regular irregularities. For the HMM 330 analysis, which is an analysis that is commonly used in the art to detect AFIB from ECG waveforms, a detailed pulse interval 312 classification is created where pulse intervals are classified as VS=very short, S=short, SS=slightly short, R=regular, SL=slightly long, L=long and VL=very long. The HMM 330 analysis requires less intervals than the contextual analysis 340 to be accurate and the specifics of the HMM 330 analysis can be found in U.S. Pat. No. 6,937,887.

While the Hidden Markov Model is known in the art to detect AFIB from an ECG waveform, utilizing the HMM 330 analysis in this system and method has never been contemplated. While the HMM 330 analysis calculates a probability of a heart rhythm being an irregular rhythm, the contextual analysis 340 utilizes a greater number of pulse intervals 314 to rule out AFIB as the source of irregularity. The contextual analysis 340 utilizes a greater number of pulse intervals 314, while only classifying the intervals as S=short or L=long. Again, the results of these two analysis contribute to determining whether the rhythm is irregularly irregular in step 370. Finally, it should be noted that the method as described herein may be embodied as a set of computer code executable by a processor in a monitoring system such as that depicted in FIG. 6.

Figure 6:
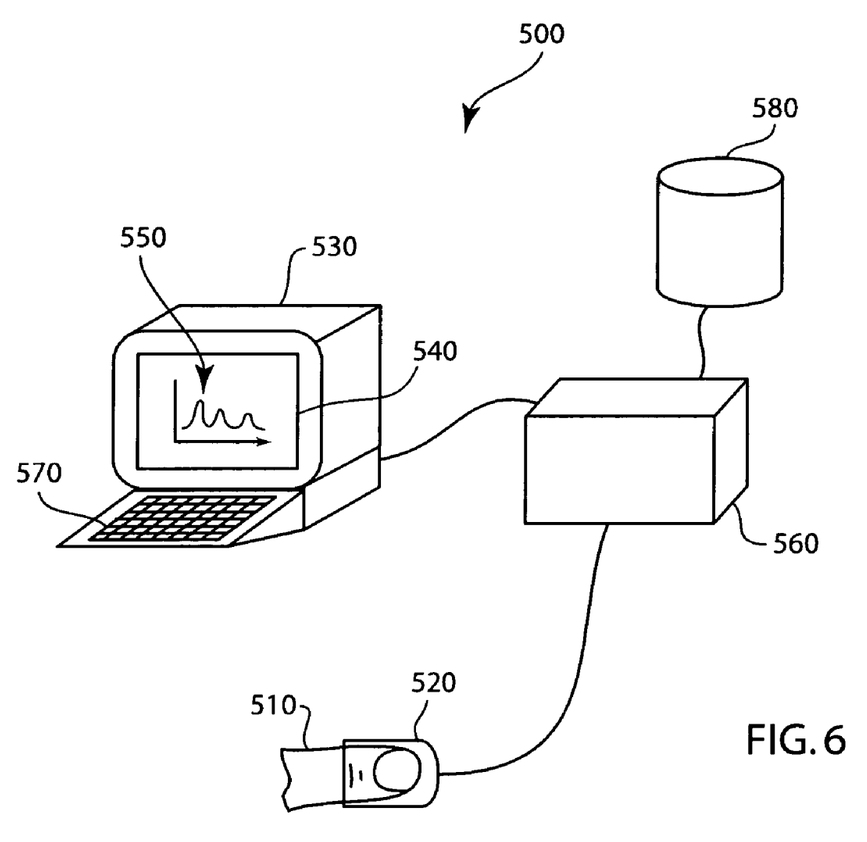
FIG. 6 illustrates a block diagram of a system in accordance with an embodiment of the present invention.

FIG. 6 depicts a detection system 500 of the present invention including a finger probe 520 that is attachable to the patient's finger 510 and configured to acquire the plethysmograph waveform from the patent's finger 510 and send that level to the processor 560 such that a plethysmographic waveform 550 can be displayed on an electronic device 530 such as a computer, hand-held device, laptop, or other electronic device 530 known in the art. The electronic device 530 includes an input device 570, such as a keyboard, so that a patient or physician, or other user of the electronic device may manipulate the display 540, configure the output from the method, or deactivate or activate alarms. The computer code embodying the method of the present invention is stored in a stored media 580 and the processor 560 is configured to execute the code. The processor 560, while executing the code, will take into account all of the factors as described above in describing the detection method 100 and determine whether the patient is in AFIB. Furthermore, the AFIB report 380 and the trend report 390 may be displayed 540.

The present invention provides numerous advantages over the prior art. The invention includes lower cost (elimination of several ECG electrodes and/or electrode contact jells) greater flexibility and ease of use over multiple ECG electrodes, shorter hook up time, and the system and method are more convenient and easier for patients to implement than ECG, meaning greater patient compliance. Patient compliance is also improved in that the acquisition time is much shorter, and the short-term measurement means that a compliant patient can minimize such things as motion artifact, which tends to make typical ECG systems less accurate.

The system and method is primarily intended as a periodic assessment tool, so real-time outputs are not necessary, and because SPO2 measurement is already a common component of patient monitoring devices, no additional hardware is required to implement the system. Detection of AFIB within 48 hours of initiation provides the opportunity for cardioversion without the substantial cost and time of anti-thrombolytic therapy, thereby improving healthcare while reducing healthcare costs. This improved system and method of improving home monitoring will also result in fewer visits to the emergency room, while reducing home nursing care and office visits by not requiring professional application of sensors, as is done in ECG applications.

These techniques could also be used in conjunction with other means of measuring blood volume or blood pressure pulses to measure the presence of AFIB. These include, but are not limited to: impedance plethysmography, optical reflectance plethysmography, arterial tonometry and piezoelectric sensors.

The present invention has been described in terms of specific embodiments incorporating details to facilitate the understanding of the principals of construction and operation of the invention. Such reference herein to specific embodiments and details thereof is not intended to limit the scope of the claims appended hereto. It will be apparent to those skilled in the art that modifications may be made in the embodiment chosen for illustration without departing from the spirit and scope of the invention.

We claim:

1. A method of detecting atrial fibrillation in a human or animal subject, the method comprising:
   acquiring a plethysmographic waveform of a patient from a monitoring device over a period of time;
   detecting a set of pulse intervals from the plethysmographic waveform;
   measuring a set of pulse features from the plethysmographic waveform; and
   analyzing the set of pulse intervals and the set of pulse features from the plethysmographic waveform to determine an atrial fibrillation state of the patient.

2. The method as claimed in claim 1, wherein the monitoring device is a pulse oximeter sensor.

3. The method as claimed in claim 1, wherein one of the set of features is a set of pulse amplitudes.

4. The method as claimed in claim 1, further comprising analyzing the set of pulse intervals and the set of pulse features from the plethysmographic waveform to detect an atrial fibrillation trend of the patient.

5. The method as claimed in claim 4, further comprising reporting the atrial fibrillation trend.

6. The method as claimed in claim 1, further comprising reporting the atrial fibrillation state.

7. The method as claimed in claim 1, wherein analyzing the set of pulse intervals includes: conducting a hidden Markov model analysis on the set of pulse intervals; and conducting a contextual analysis on the set of pulse intervals.

8. The method as claimed in claim 7, wherein the hidden Markov model analysis determines a probability of the patient having an irregular heart rhythm.

9. The method as claimed in claim 7, wherein the contextual analysis rules out atrial fibrillation as a source of irregular heart rhythm.

10. The method as claimed in claim 1, wherein analyzing the set of pulse features includes:
    calculating amplitude variation between each consecutive one of the set of pulse amplitudes.

11. The method as claimed in claim 10, wherein the atrial fibrillation state determination is dependent on an analysis of pulse amplitude variation.

12. The method as claimed in claim 1, wherein analyzing the set of pulse amplitudes includes determining a set of filling time dynamics of the set of pulse amplitudes.

13. The method as claimed in claim 12, wherein the steps of analyzing the set of pulse amplitudes and determining the set of filling time dynamics provides an indication of the degree of atrial augmentation present.

14. A system for detecting atrial fibrillation in a human or animal subject, the system comprising:
    a remote sensing system configured to analyze a plethysmographic waveform from a monitoring device;
    a storage media for storing a computer application;
    a processing unit coupled to the remote sensing system and the storage media, and configured to execute the computer application, and further configured to receive the plethysmographic waveform from the remote sensing system,
    wherein when the computer application is executed, a set of pulse intervals from the plethysmographic waveform are detected and a set of pulse features are measured from the plethysmographic waveform, and further wherein the set of pulse intervals and the set of pulse features are analyzed to determine an atrial fibrillation state of the patient.

15. The system as claimed in claim 14, wherein the monitoring device is a pulse oximeter sensor.

16. The system as claimed in claim 14, further wherein when the set of pulse intervals and the set of pulse features from the plethysmographic waveform are analyzed, an atrial fibrillation trend of the patient is detected.

17. The system as claimed in claim 16, further comprising means for reporting the atrial fibrillation trend to the patient.

18. The system as claimed in claim 14, further comprising means for reporting the atrial fibrillation state.

19. The system as claimed in claim 14, wherein when the computer application is executed and the set of pulse intervals is analyzed, a hidden Markov model analysis is conducted on the set of pulse intervals, and a contextual analysis is conducted on the set of pulse intervals.

20. The system as claimed in claim 19, wherein the hidden Markov model analysis determines a probability of the patient having an irregular heart rhythm.

21. The system as claimed in claim 19, wherein the contextual analysis rules out atrial fibrillation as a source of irregular heart rhythm.

22. The system as claimed in claim 14, wherein when the computer application is executed and the set of pulse features is analyzed, the filling time dynamics of the set of pulse features is determined, and feature variation between each one of the set of pulse features is calculated relative to the mean, the median, consecutive pulses, or maximum to minimum.

23. The system as claimed in claim 22, wherein the atrial fibrillation state determination is dependent on an analysis of pulse amplitude variation.

24. The system as claimed in claim 23, wherein the analysis of pulse amplitude variation as a function of filling time provides an indication of the degree of atrial augmentation present.

25. A method of detecting atrial fibrillation, the method comprising:
    producing a plethysmographic waveform from a plethysmographic sensor;
    detecting a set of pulse intervals from the plethysmographic waveform;
    measuring a set of pulse features from the plethysmographic waveform;
    analyzing the set of pulse intervals and the set of pulse features from the plethysmographic waveform to determine an atrial fibrillation state of the patient and to detect an atrial fibrillation trend of the patient; and
    reporting the atrial fibrillation state and the atrial fibrillation trend to the patient,
    wherein analyzing the set of pulse intervals includes conducting a hidden Markov model analysis on the set of pulse intervals, and conducting a contextual analysis on the set of pulse intervals, and
    further wherein analyzing the set of pulse amplitudes includes determining the filling time dynamics of the set of pulse amplitudes, and calculating amplitude variation between each one of the set of pulse amplitudes relative to the mean, the median, consecutive pulses, or maximum to minimum.

26. The method as claimed in claim 25, wherein the monitoring device is a pulse oximeter sensor.

* * * * *